(12) United States Patent
Hennig

(10) Patent No.: US 8,068,941 B2
(45) Date of Patent: Nov. 29, 2011

(54) USER-CONTROLLABLE POWER-ASSISTED SYSTEM AND METHOD FOR THE APPLICATION OF PRESSURE

(75) Inventor: Don B. Hennig, Gales Creek, OR (US)

(73) Assignee: Bio-Applications, LLC, Portland, OR (US)

( * ) Notice: Subject to any disclaimer, the term of this patent is extended or adjusted under 35 U.S.C. 154(b) by 1387 days.

(21) Appl. No.: 11/609,329

(22) Filed: Dec. 11, 2006

(65) Prior Publication Data

US 2007/0236081 A1    Oct. 11, 2007

Related U.S. Application Data

(60) Provisional application No. 60/781,188, filed on Mar. 9, 2006.

(51) Int. Cl.
*G05D 23/00* (2006.01)
*G05B 19/00* (2006.01)
*B60T 13/46* (2006.01)
*B60T 8/60* (2006.01)

(52) U.S. Cl. ............ 700/301; 700/260; 303/4; 303/155

(58) Field of Classification Search ................. 700/301; 303/114.3, 14, 155
See application file for complete search history.

(56) References Cited

U.S. PATENT DOCUMENTS

| 5,553,618 | A | 9/1996 | Suzuki et al. | |
| 6,796,447 | B2* | 9/2004 | Laundry et al. | 212/275 |
| 2004/0254048 | A1* | 12/2004 | Yone | 477/108 |
| 2005/0154295 | A1* | 7/2005 | Quistgaard et al. | 600/424 |
| 2005/0193451 | A1 | 9/2005 | Quistgaard et al. | |
| 2007/0001508 | A1* | 1/2007 | Schluter | 303/114.3 |

\* cited by examiner

*Primary Examiner* — Albert Decady
*Assistant Examiner* — Sivalingam Sivanesan
(74) *Attorney, Agent, or Firm* — Joseph P. Curtin, L.L.C.

(57) ABSTRACT

A system and a method for a controllable power-assisted application of pressure includes a force sensor capable of sensing a user-applied force; and a force generator responsive to the sensed user-applied force and capable of generating a force that is applied to a pressure-applying device. A force magnitude of the force applied to the pressure-applying device is based on a magnitude of the sensed user-applied force. One embodiment provides that the force applied to the pressure-applying device by the force generator exerts a predetermined amount of pressure against a surface. Another embodiment provides that the force magnitude is greater than a magnitude of the sensed user-applied force. Yet another embodiment provides that the force magnitude is proportional to a magnitude of the sensed user-applied force.

20 Claims, 3 Drawing Sheets

USER-CONTROLLABLE POWER-ASSISTED SYSTEM AND METHOD FOR THE APPLICATION OF PRESSURE

CROSS-REFERENCE TO RELATED APPLICATION

The present patent application claims priority to U.S. Provisional Patent Application Ser. No. 60/781,188, filed Mar. 9, 2006, entitled "User-Controllable Power-Assisted Handling System and Method," and invented by Don B. Hennig, the disclosure of which is incorporated by reference herein.

BACKGROUND

The subject matter disclosed herein relates to a system and method for a power-assisted application of pressure. More particularly, the subject matter disclosed herein relates to a system and a method for a controllable power-assisted application of pressure.

BRIEF DESCRIPTION OF THE DRAWINGS

The subject matter disclosed herein is illustrated by way of example and not by limitation in the accompanying figures in which like reference numerals indicate similar elements and in which.

DETAILED DESCRIPTION

The word "exemplary" is used herein to mean "serving as an example, instance, or illustration." Any embodiment described herein as "exemplary" is not to be construed as necessarily preferred or advantageous over other embodiments. The words "transducer" and "transducer head" are used herein to mean "a device that is actuated by power and/or energy from one system and supplies power and/or energy usually in another form to a second system." Additionally, it should be understood that the words "transducer" and "transducer head" include bidirectional transducer devices.

The subject matter disclosed herein relates to a controllable power-assisted system and method for the application of pressure. In one exemplary embodiment, the subject matter disclosed herein provides a controllable power-assisted sonographic system (also commonly known as an ultrasound system) that allows an operator (or user), such as a physician or a sonogram technician, to apply about 50 pounds of pressure to a selected area of a prone patient in response to a hand-guided force of about 2-8 pounds of pressure. In another exemplary embodiment, the subject matter disclosed herein allows an operator to apply between about 0-8 pounds of pressure through a sonographic transducer head or a sonogram transducer head coupling device, which is assisted by the subject matter disclosed herein to deliver between about 0 pounds of pressure to a maximum of about 40 pounds of pressure, as guided by the operator.

Figure 1:
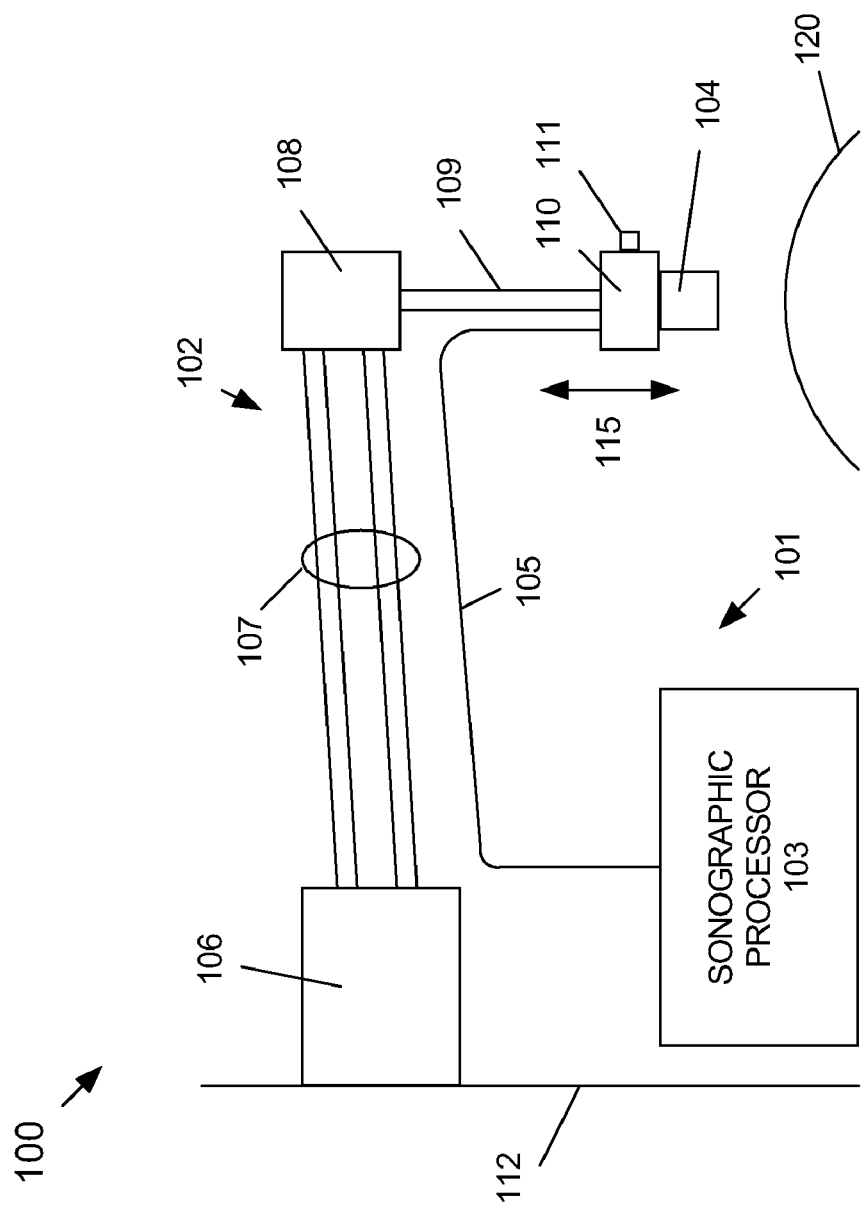
FIG. 1 depicts a functional block diagram of one exemplary embodiment of a system for providing a controllable power-assisted application of pressure to the subject matter disclosed herein.

FIG. 1 depicts a functional block diagram of one exemplary embodiment of a system 100 for providing a controllable power-assisted application of pressure according to the subject matter disclosed herein. System 100 includes sonographic processing equipment 101 and a controllable, power-assist device 102. Controllable power-assist device 102 generates a controllable force in a near vertical direction 115 that can be used for applying a pressure-applying device, such as a transducer head, against soft tissue of a prone patient, a portion of which is indicated at 120, with a desired level of uniform and sustained pressure.

Sonographic processing equipment 101 includes a processor 103 and a pressure-applying device 104, which is coupled to processor 103 in a well-known manner through a cable or wire 105. Alternatively, pressure-applying device 104 could be coupled to processor 103 in a well-known manner using a wireless link. For many of the exemplary embodiments of the subject matter disclosed herein, pressure-applying device 104 comprises a sonographic (ultrasound) transducer head and will be described as such. It should be understood, though, that pressure-applying device 104 is not limited to being a sonographic transducer head and could alternatively be a transducer head, a radiographic transducer head, an x-ray head, a sterilizing transducer head, an instrumentation head and/or a device used for penetrating soft materials and/or tissue.

Processor 103 can include the necessary components and/or algorithms for processing sonographic signals received by transducer head 104 and the necessary components for displaying sonographic information and/or outputting sonographic information to another processing device. Each of processor 103, transducer head 104 and cable 105 can be readily available sonographic devices and/or components. Alternatively, any one of processor 103, transducer head 104 and cable 105 could be adapted for a special sonographic application.

Power-assist device 102 includes a force generator 106, a power-assist arm 107, a coupling member 108, a coupling member 109, a coupling device 110, and an operator-applied-force sensor 111 for controlling the power-assisted force generated by power-assist device 102. In one exemplary embodiment, coupling device 110 is coupled to power-assist arm 107 and coupling member 108 without using coupling member 109. In another exemplary embodiment, coupling device 110 is coupled directly to force generator 106. In yet another exemplary embodiment, pressure-applying device 104 is coupled directly to force generator 106. Power-assist arm 107 is depicted in FIG. 1 as a four-bar parallelogram-linkage-type power assist arm that operates in a well-known manner to impart a controlled force to coupling device 110. Alternatively, power-assist arm 107 can be configured as a single-bar-type power assist arm.

In one exemplary embodiment, force generator 106 is a controllable pneumatic force generator that operates in a well-known manner for generating a force that is coupled in a well-known manner to power-assist arm 107 and through power-assist arm 107, coupling arm 108, and coupling member 109 to coupling device 110. In another exemplary embodiment, force generator 106 could be a controllable hydraulic force generator that operates in a well-known manner for generating a force that is coupled in a well-known manner to power-assist arm 107 and through power assist arm 107, coupling arm 108 and coupling member 109 to coupling device 110. In still another exemplary embodiment, force generator 106 could be a controllable electric servo motor or stepper motor that operates in a well-known manner for generating a force that is coupled in a well-known manner to power-assist arm 107 and through power assist arm 107, coupling arm 108 and coupling member 109 to coupling device 110. In one exemplary embodiment, force generator 106 includes a controller, such as a state machine formed from, for example, discrete logic, that controls the functional operation of force generator 106 by responding to sensor 111, as described below, and for providing safety features. In another exemplary embodiment, force generator 106 includes a programmable controller, such as a programmable microcontroller or programmable microprocessor, that controls the functional operation of force generator 106 by responding to sensor 111, as described below, and for providing safety features.

Operator-applied-force sensor 111 senses a force that an operator applies to pressure-applying device 104 as the operator hand-guides pressure-applying device 104 and generates a signal corresponding to the sensed force. In one exemplary embodiment, sensor 111 is embodied as a pressure-sensitive switch that senses the amount of pressure an operator places on sensor 111 as the operator hand-guides transducer head 104 toward patient 120 or a desired target. Alternatively, sensor 111 could be configured to sense the pressure created between coupling device 110 and transducer head 104 when the operator hand-guides transducer head 104 toward patient 120 or a desired target. As yet another alternative, sensor 111 could be a pressure switch that is actuated by an operator when the operator applies a predetermined amount of force or pressure to the pressure switch. Sensor 111 accordingly generates a signal corresponding to the amount of sensed pressure and that is coupled to force generator 106 in a well-known manner, such as, but not limited to, a wired connection or a wireless connection. In response to the signal generated by sensor 111, force generator 106 generates a force that is applied to power-assist arm 107, thereby lowering transducer head 104 toward patient 120 or a desired target, thereby assisting the hand-guided motion the operator is applying to transducer head 104. In one exemplary embodiment, when an operator applies pressure to either transducer head 104 or directly to a sensor 111, force generator 106 is responsive to the magnitude of pressure sensed by sensor 111 and generates a force that is related to and greater than the magnitude of the pressure sensed by sensor 111. In one embodiment, the force generated by force generator 106 is proportional to the magnitude of the pressure sensed by sensor 111. When transducer head 104 comes into contact with patient 120 or a desired target, force generator 106 generates a force that is applied to transducer 104 through power-assist arm 107 so that transducer 104 contacts the patient with sufficient uniform and sustained pressure to produce a sonographic image with sonographic processing equipment 101. That is, force generator 106 amplifies the force sensed by sensor 111 to a predetermined amount to produce a sonographic image with sonographic processing equipment 101.

In one exemplary embodiment, force generator 106 generates about 0 pound of pressure to a maximum of about 40 pounds of pressure in response to a sensed pressure of between about 0-8 pounds of pressure. In another exemplary embodiment, force generator 106 generates about a 50 pounds of pressure through power-assist arm 107 to a selected area of prone patient 120 in response to a hand-guided force of about 2-8 pounds of pressure. In yet other exemplary embodiments, force generator 106 can be configured to generate a selected amplified minimum and maximum force in response to a selected range of pressure sensed by sensor 111.

Coupling device 110 provides a mechanical coupling between pressure-applied device 104, power-assist arm 107, coupling member 108 and coupling member 109 (when included). In one exemplary embodiment, coupling device 110 could be provided by screw-band-type hose clamps having a sufficient diameter for operatively receiving transducer head 104. In another exemplary embodiment, coupling device 110 could releasably hold a transducer head 104 so that the transducer head could be used coupled to power-assist arm 107 or in a free-hand manner depending on the specific procedure being performed. In yet another exemplary embodiment, a second transducer head 104 (not shown in FIG. 1) could be simultaneously coupled to processor 103 of sonographic processing equipment 101 through a cable (also not shown).

In one exemplary embodiment, power-assist arm 107 includes a section that allows transducer head 104 (i.e., pressure-applying device 104) to be oriented horizontally so that a side sonographic image of a patient can be produced. For this exemplary embodiment, when transducer head 104 is horizontally oriented, sensors, such as position sensors and/or contact sensors (not shown in FIG. 1), sense the orientation of transducer head 104 and disengage force generator 106 so that power-assist arm 107 can be freely positioned around a patient and so that force generator 106 does not generate a force. In one exemplary embodiment, the position sensors and/or contact sensors sense the position of transducer head 104 when transducer head 104 is rotated past about 20-30 degrees from vertical orientation and disengage force generator 106. In another exemplary embodiment, when the sensors sense that transducer head 104 is rotated past about 20-30 degrees from vertical orientation, force generator 106 is controlled to reduce the force generated, for example, in proportion to the amount of sensed rotation from a predetermined orientation, such as vertical, or as a sinusoidal-based decay function based on the amount of sensed rotation from a predetermined orientation.

Figure 2:
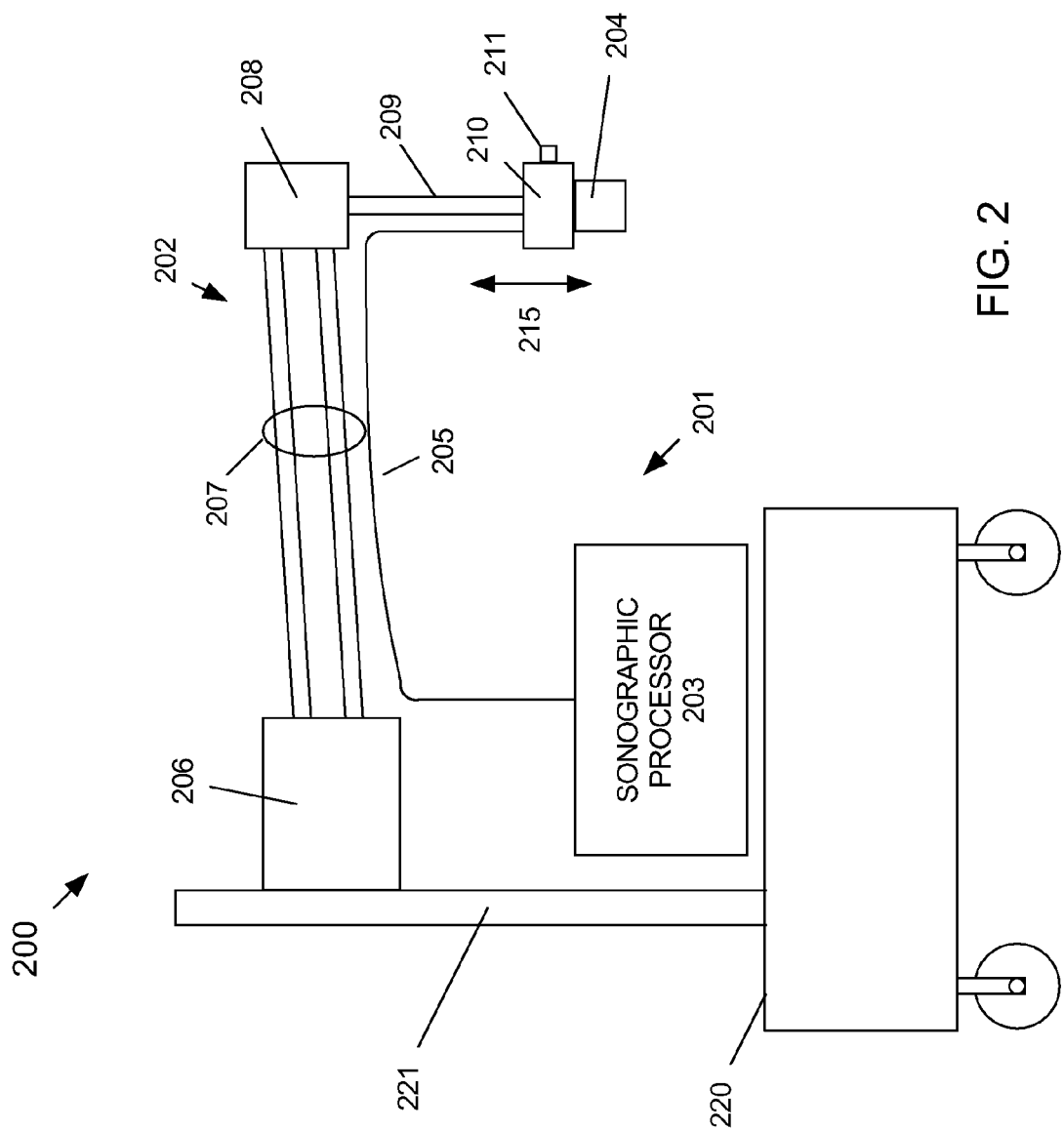
FIG. 2 depicts a functional block diagram of an alternative exemplary embodiment of a system that is part of a mobile cart and that can be positioned where desired for performing a controllable power-assisted application of pressure procedure according to the subject matter disclosed herein.

Power-assist device 102 is depicted in FIG. 1 as being fastened to a fixed structure 112, such as a wall or a pole. FIG. 2 depicts a functional block diagram of an alternative exemplary embodiment of a system 200 that is part of a mobile device 220, such as a cart, and that can be positioned where desired for performing a controllable power-assisted application of pressure according to the subject matter disclosed herein. System 200 is configured similar to system 100, shown in FIG. 1, and includes sonographic processing equipment 201 and a controllable, power-assist device 202. Controllable power-assist device 202 generates a controllable force in a near vertical direction 215 that can be used for applying a transducer head against soft tissue of a prone patient (not shown in FIG. 2).

FIG. 2 depicts sonographic processing equipment 201 includes a processor 203 and pressure-applying device 204, such as a sonographic head, which is coupled to processor 203 in a well-known manner through a cable or wire 205. Alternatively, pressure-applying device 204 could be coupled to processor 203 in a well-known manner using a wireless link. For this and many of the exemplary embodiments of the subject matter disclosed herein, pressure-applying device 204 comprises a sonographic (ultrasound) transducer head and will be described as such. It should be understood, though, that pressure-applying device 204 is not limited to being a sonographic transducer head and could alternatively be a transducer head, a radiographic transducer head, an x-ray head, a sterilizing transducer head, an instrumentation head and/or a device used for penetrating soft materials and/or tissue. Processor 203 can include the necessary components and/or algorithms for processing sonographic signals received by transducer head 204 and the necessary components for displaying sonographic information and/or outputting sonographic information to another processing device.

Power-assist device 202 includes a force generator 206, a power-assist arm 207, a coupling member 208, a coupling member 209, a coupling device 210, and an operator-applied-force sensor 211 for controlling the power-assisted force generated by power-assist device 202. In one exemplary embodiment, coupling device 210 is coupled to power-assist arm 207 and coupling member 208 without using coupling member 209. In another exemplary embodiment, coupling device 210 is coupled directly to force generator 206. In yet another exemplary embodiment, pressure-applying device 204 is coupled directly to force generator 206. Power-assist arm 207 is depicted in FIG. 2 as a four-bar parallelogram-linkage-type power assist arm that operates in a well-known manner to impart a controlled force to coupling device 210. Alternatively, power-assist arm 207 can be configured as a single-bar-type power assist arm. Mobile cart 220 includes a mounting member 221 to which system 200 is mounted in a well-known manner.

Operator-applied-force sensor 211 senses a force that an operator applies to pressure-applying device 204 as the operator hand-guides pressure-applying device 204 and generates a signal corresponding to the sensed force. In one exemplary embodiment, sensor 211 is embodied as a pressure-sensitive switch that senses the amount of pressure an operator places on sensor 211 as the operator hand-guides transducer head 204 toward a patient or a desired target. Alternatively, sensor 211 could be configured to sense the pressure created between coupling device 210 and transducer head 204 when the operator hand-guides transducer head 204 toward a patient or a desired target. As yet another alternative, sensor 211 could be a pressure switch that is actuated by an operator when the operator applies a predetermined amount of force or pressure to the pressure switch. Sensor 211 accordingly generates a signal corresponding to the amount of sensed pressure and that is coupled to force generator 206 in a well-known manner, such as, but not limited to, a wired connection or a wireless connection. In response to the signal generated by sensor 211, force generator 206 generates a force that is applied to power-assist arm 207, thereby lowering transducer head 204 toward a patient or a desired target, thereby assisting the hand-guided motion the operator is applying to transducer head 204. In one exemplary embodiment, when an operator applies pressure to either transducer head 204 or directly to a sensor 211, force generator 206 is responsive to the magnitude of pressure sensed by sensor 211 and generates a force that is related to and greater than the magnitude of the pressure sensed by sensor 211. In one embodiment, the force generated by force generator 206 is proportional to the magnitude of the pressure sensed by sensor 211. When transducer head 204 comes into contact with a patient or a desired target, force generator 206 generates a force that is applied to transducer 204 through power-assist arm 207 so that transducer 204 contacts the patient or the desired target with sufficient uniform and sustained pressure to produce a sonographic image with sonographic processing equipment 201. That is, force generator 206 amplifies the force sensed by sensor 211 to a predetermined amount to produce a sonographic image with sonographic processing equipment 201.

Figure 3:
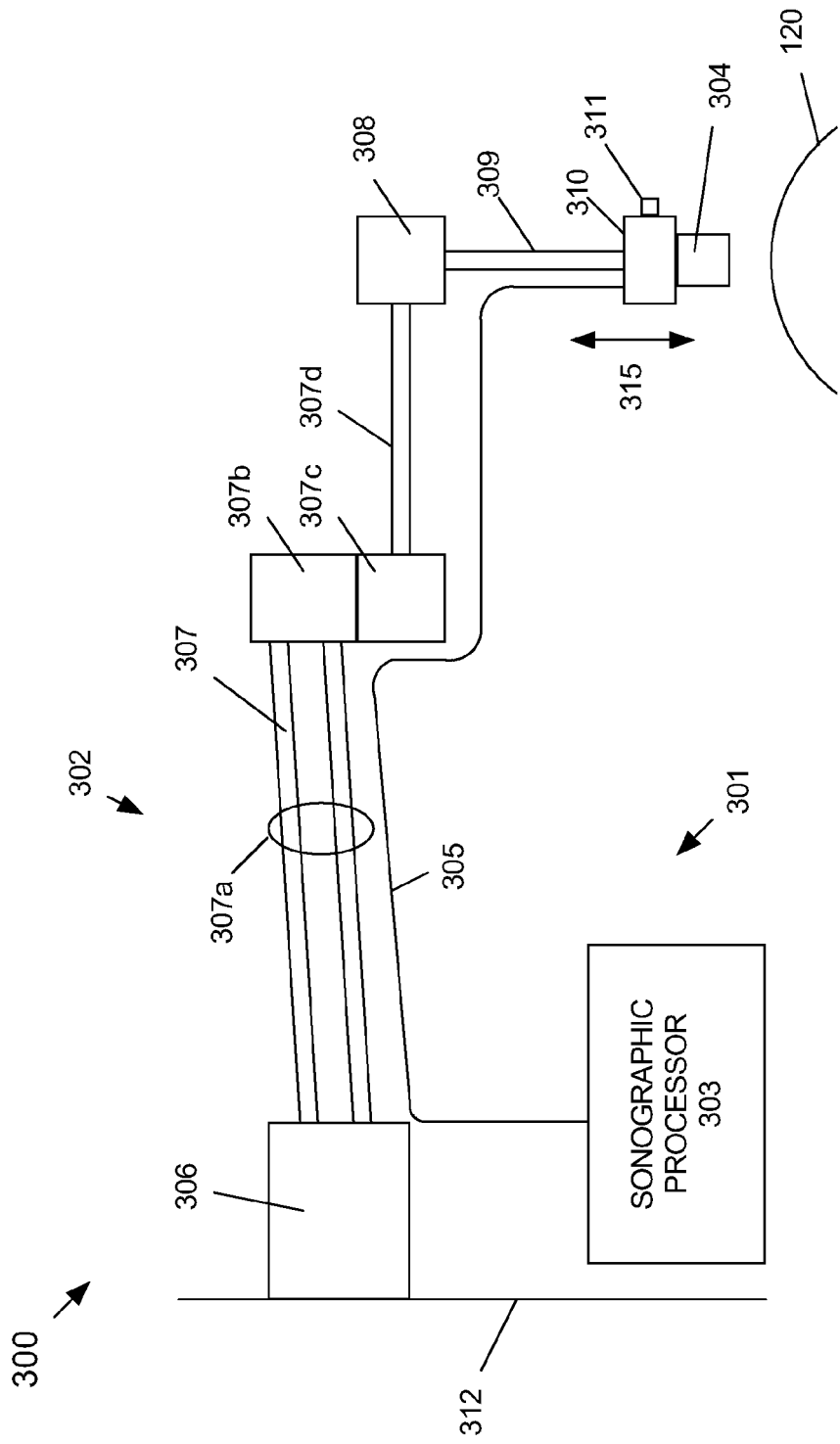
FIG. 3 depicts a functional block diagram of another exemplary embodiment of a system for providing a controllable power-assisted application of pressure procedure according to the subject matter disclosed herein.

FIG. 3 depicts a functional block diagram of another exemplary embodiment of a system 300 for providing a controllable power-assisted application of pressure that can be positioned to, for example, a desired horizontal position within a selected area that is, for example, about two square feet and also provides, for example, about a 30 inch vertical travel 315 for transducer head 304 according to the subject matter disclosed herein. System 300 includes sonographic processing equipment 301 and a controllable, power-assist device 302. Controllable power-assist device 302 generates a controllable force that can be used for applying a transducer head against soft tissue of a prone patient 120.

Sonographic processing equipment 301 includes a processor 303 and pressure-applying device 304, which is coupled to processor 303 in a well-known manner through a cable or wire 305. Alternatively, transducer head 304 could be coupled to processor 303 in a well-known manner using a wireless link. For this and many of the exemplary embodiments of the subject matter disclosed herein, pressure-applying device 304 comprises a sonographic (ultrasound) transducer head and will be described as such. It should be understood, though, that pressure-applying device 304 is not limited to being a sonographic transducer head and could alternatively be a transducer head, a radiographic transducer head, an x-ray head, a sterilizing transducer head, an instrumentation head and/or a device used for penetrating soft materials and/or tissue. Processor 303 can include the necessary components and/or algorithms for processing sonographic signals received by transducer head 304 and the necessary components for displaying sonographic information and/or outputting sonographic information to another processing device. Each of processor 303, transducer head 304 and cable 305 can be readily available sonographic devices and/or components. In another alternative embodiment, any one of processor 303, transducer head 304 and cable 305 could be adapted for a special sonographic application.

Power-assist device 302 includes a force generator 306, a power-assist arm 307, a coupling member 308, a coupling member 309, a coupling device 310, and an operator-applied-force sensor 311 for controlling the power-assisted force generated by power-assist device 302. In one exemplary embodiment, coupling device 310 is coupled to power-assist arm 307 and coupling member 308 without using coupling member 309. Power-assist arm 307 comprises a four-bar parallelogram-linkage-type arm portion 307a that is operatively coupled to rotary-type joint 307b, 207c that is operatively coupled to single-bar-type arm 307d, which in turn is operatively coupled to coupling member 308. Rotary-type joint 307b, 307c operates in a well-known manner to allow joint portion 307c to rotate with respect to joint portion 307b. Power-assist arm 307 operates in a well-known manner to impart a controlled force to coupling device 3 10. Alternatively, power-assist arm 307 could be configured so that four-bar parallelogram-linkage arm portion 307a and single-bar arm portion 307d are interchanged. As yet another alternative, power assist arm 307 could have two or more four-bar parallelogram-linkage arm portions 307a and/or two or more single-bar arm portions 307d. Operator-applied-force sensor 311 operates in a manner similar to operator-applied-force sensors 111 and 211.

Power-assist device 302 is depicted in FIG. 3 as being fastened to a fixed structure 312, such as a wall or a pole. Alternatively, power-assist device 302 could be mounted on a mobile device, such as a cart, similar to that depicted in FIG. 2.

The subject matter disclosed herein further includes safety features that limit the pressure applied to a patient in a well-known manner, such as by pressure sensors that detect the pressure being applied to a patient and/or by pressure sensors that can determined the amount of pressure being applied to a patient based on the amount of pressure developed by force generator 106. Additional safety features that can be included with the subject matter disclosed herein include a release mechanism that allows, for example, power-assist arm 107 to be released and moved away from a patient when, for example, pressure sensors detect the pressure being applied to a patient to exceed a predetermined pressure level.

One exemplary embodiment of the subject matter disclosed herein provides a transducer-coupling device having a gripping surface of about 1.25" diameter that may includes a pressure-sensitive switch. For this exemplary embodiment, an operator must actuate and hold the switch in order for the force generator and arm brakes to be active in a well-known manner. When the pressure-sensitive switch in not actuated, the power-assist arm floats free, thereby allowing a plurality of modes of operation.

According to yet another exemplary embodiment of the subject matter disclosed herein, an operator positions the transducer head on a selected location on the body of a patient and orients the transducer head at a desired "target". The operator then activates the power-assist device portion of the system by applying pressure to the pressure-sensitive switch and simply pushing the transducer head toward the target, thereby causing the power-assist arm to push the transducer head further into the body of the patient. For this exemplary embodiment, the power-assist device portion is gimbaled and allows about 5 degrees of pivot in any direction, thereby allowing an operator a small amount of side to side movement in order to get a better view of the target. To allow more travel in any the x, y or z directions, the operator releases the pressure-sensitive switch, which, in turn, releases the arm brake and the force generator, thereby allowing the whole assembly to be repositioned. In still another exemplary embodiment of the present invention, the power-assist portion of the system provides x, y and z axes directions of travel while applying pressure to a patient.

One exemplary application of the subject matter disclosed herein is in a semi-clean environment such as a physician's, a hospital or clinic-type examination room. Another exemplary application of the subject matter disclosed herein is in a semi-clean environment such a veterinary large-animal examination facility. Yet another exemplary application for which the subject matter disclosed herein could be used is for applying an inspection device to a soft material or tissue, such as meat. The subject matter disclosed herein is also suitable for providing hand-guided uniform and sustained pressure for a radiographic application, an x-ray, a sterilization application and/or an instrumentation application. Still another exemplary application for which the subject matter disclosed herein could be used is for applying a force to a penetrating device in order to penetrate a material or target with a predetermined amount of force or pressure. For any of the exemplary applications for which the subject matter disclosed herein may be used, the subject matter disclosed herein could be configured so that the power-assisted application of pressure could be in a horizontal direction depending upon the specific application. Alternatively, the subject matter disclosed herein could be configured so that the power-assisted application of pressure could be in a direction that is substantially the same direction in which the operator-applied force is applied.

Although the foregoing disclosed subject matter has been described in some detail for purposes of clarity of understanding, it will be apparent that certain changes and modifications may be practiced that are within the scope of the appended claims. Accordingly, the present embodiments are to be considered as illustrative and not restrictive, and the subject matter disclosed herein is not to be limited to the details given herein, but may be modified within the scope and equivalents of the appended claims.

What is claimed is:

1. A system, comprising:
a pressure-applying device;
a force sensor capable of sensing a first user-applied force; and
a force generator responsive to the sensed first user-applied force and capable of generating a force that is applied to the pressure-applying device in a direction that is substantially in a same direction that a second user-applied force is applied to the pressure-applying device as the pressure-applying device is hand guided to contact and apply pressure to a surface, a magnitude of the force applied to the pressure-applying device by the force generator being greater than a magnitude of the second user-applied force that is applied to the pressure-applying device as the pressure-applying device is hand guided to contact and apply pressure to the surface.

2. The system according to claim 1, wherein the force applied to the pressure-applying device by the force generator exerts a predetermined amount of pressure to the surface in contact with the pressure-applying device.

3. The system according to claim 1, wherein the second user-applied force corresponds to about 2-8 pounds of pressure, and the force generated by the force generator corresponds to about 50 pounds of pressure applied to the surface.

4. The system according to claim 3, wherein the first user-applied force and the second user-applied force are the same.

5. The system according to claim 4, wherein the pressure-applying device comprises a transducer head, a sonographic transducer head, a radiographic transducer head, an x-ray head, a sterilizing transducer head, an instrumentation head, or a material penetrating device.

6. The system according to claim 1, wherein the magnitude of the force generated by the force generator is proportional to a magnitude of the sensed first user-applied force.

7. The system according to claim 6, wherein the sensed first user-applied force corresponds to about 0-8 pounds of pressure, and the force generated by the force generator corresponds proportionally to about 0-40 pounds of pressure.

8. The system according to claim 7, wherein the first user-applied force and the second user-applied force are the same.

9. The system according to claim 8, wherein the pressure-applying device comprises a transducer head, a sonographic transducer head, a radiographic transducer head, an x-ray head, a sterilizing transducer head, an instrumentation head, or a material penetrating device.

10. The system according to claim 1, wherein the pressure-applying device comprises a transducer head, a sonographic transducer head, a radiographic transducer head, an x-ray head, a sterilizing transducer head, an instrumentation head, or a material penetrating device.

11. The system according to claim 10, wherein the force applied to the pressure-applying device by the force generator exerts a predetermined amount of pressure to the surface in contact with the pressure-applying device.

12. A method, comprising:
sensing a first user-applied force; and
generating a force in response to the sensed first user-applied force; and
applying the generated force to a pressure-applying device in a direction that is substantially in a same direction that a second user-applied force is applied to the pressure-applying device as the pressure-applying device is hand guided to contact and apply pressure to a surface, a magnitude of the force applied to the pressure-applying device being greater than a magnitude of the second user-applied force that is applied to the pressure-applying device as the pressure-applying device is hand guided to contact and apply pressure to the surface.

13. The method according to claim 12, wherein the generated force applied to the pressure-applying device exerts a predetermined amount of pressure to the surface in contact with the pressure-applying device.

14. The method according to claim 12, wherein the second user-applied force corresponds to about 2-8 pounds of pressure, and the generated force corresponds to about 50 pounds of pressure applied to the surface.

15. The method according to claim 14, wherein the first user-applied force and the second user-applied force are the same.

16. The method according to claim 12, wherein the magnitude of the generated force is proportional to a magnitude of the sensed first user-applied force.

17. The method according to claim 16, wherein the sensed first user-applied force corresponds to about 0-8 pounds of pressure, and the generated force corresponds proportionally to about 0-40 pounds of pressure.

18. The method according to claim 17, wherein the first user-applied force and the second user-applied force are the same.

19. The method according to claim 12, wherein the pressure-applying device comprises a transducer head, a sonographic transducer head, a radiographic transducer head, an x-ray head, a sterilizing transducer head, an instrumentation head, or a material penetrating device.

20. The method according to claim 19, wherein the generated force applied to the pressure-applying device exerts a predetermined amount of pressure to the surface in contact with the pressure-applying device.

* * * * *